United States Patent [19]

Kostopoulos

[11] Patent Number: 5,766,235
[45] Date of Patent: Jun. 16, 1998

[54] APPARATUS FOR PROVIDING COOLING TO A HUMAN BODY

[76] Inventor: Thomas J. Kostopoulos, 4141 W. Wellington, Chicago, Ill. 60641

[21] Appl. No.: 799,309

[22] Filed: Feb. 18, 1997

[51] Int. Cl.⁶ .................................................. A61F 7/00
[52] U.S. Cl. ..................... 607/114; 607/108; 607/111; 607/112; 62/530; 383/901
[58] Field of Search .............................. 607/108, 109, 607/111, 112, 114; 62/530; 165/46; 383/901

[56] References Cited

U.S. PATENT DOCUMENTS

| | | | |
|---|---|---|---|
| 4,190,054 | 2/1980 | Brennan | 128/402 |
| 4,586,507 | 5/1986 | Nangle | 128/403 |
| 4,832,030 | 5/1989 | De Canto | 128/380 |
| 4,858,259 | 8/1989 | Simmons et al. | 607/114 |
| 5,000,176 | 3/1991 | Daniel | 607/108 |
| 5,179,942 | 1/1993 | Drulias et al. | 607/108 |
| 5,336,708 | 8/1994 | Chen | 524/474 |
| 5,423,875 | 6/1995 | Kehe | 607/112 |
| 5,484,366 | 1/1996 | Wilkinson | 607/114 |
| 5,514,170 | 5/1996 | Mauch | 607/114 |

*Primary Examiner*—Lee S. Cohen
*Assistant Examiner*—David M. Ruddy
*Attorney, Agent, or Firm*—David L. Volk

[57] ABSTRACT

A shallow pouch comprises a broad bottom panel, a plurality of narrow side panels, and a closable flap opposite the bottom panel. The flap includes a plurality of fasteners configured to releasably fasten the flap in a closed position over the pouch. The pouch is adapted to receive a cooling pack therein such that the cooling pack rests on the bottom panel between the side panels and such that the flap covers the cooling pack when the flap is in a closed position over the pouch. A strap is attached to the pouch and includes a strap fastening means adapted to releasably fasten the strap about a human wrist such that the bottom panel rests against an inside of the wrist.

3 Claims, 2 Drawing Sheets

APPARATUS FOR PROVIDING COOLING TO A HUMAN BODY

BACKGROUND OF THE INVENTION

1. Field of the Invention

The present invention relates to therapeutic devices for cooling body parts, particularly to devices intended to hold a cooling pack and adapted to be worn on a human appendage.

2. Description of the Related Art

When participating in demanding physical activity such as sports, gardening and construction, it is desirable to employ some kind of cooling relief to the body. To date, there has been no device specifically adapted for keeping the inside of a user's wrists cool during exercise. Such a device would be particularly advantageous if it were easily attached to and released from a person's wrists, using releasably fastenable straps.

SUMMARY OF THE INVENTION

The apparatus for providing cooling to a human body of the present invention includes a shallow pouch having a broad bottom panel, a plurality of narrow side panels, and a closable flap opposite the bottom panel. The flap includes a plurality of fasteners configured to releasably fasten the flap in a closed position over the pouch. The pouch is adapted to receive a cooling pack therein such that the cooling pack rests on the bottom panel between the side panels and such that the flap covers the cooling pack when the flap is in a closed position over the pouch. A strap is attached to the pouch and includes a strap fastening means adapted to releasably fasten the strap about a human wrist such that the bottom panel rests against an inside of the wrist.

DETAILED DESCRIPTION

Figure 1:
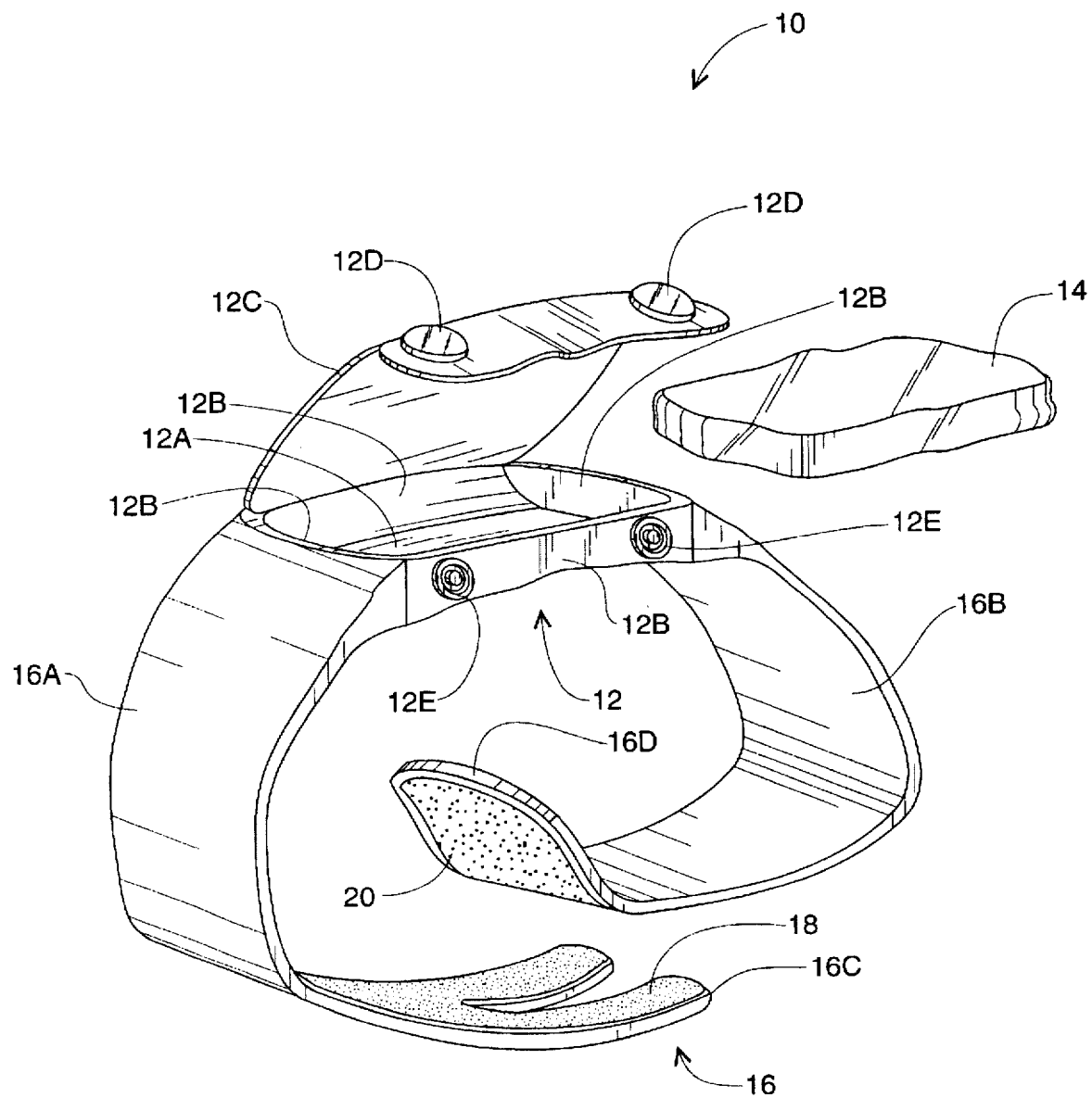
FIG. 1 is a perspective view of a cooling device.

FIG. 1 is a perspective view of a cooling device 10 comprising a shallow pouch 12 having a broad bottom panel 12A, a plurality of narrow side panels 12B, and a closable flap 12C opposite the bottom panel 12A. The flap 12C includes snap first parts 12D configured to releasably attach to snap second parts 12E on the pouch 12 in a conventional manner, thus releasably fastening the flap 12C in a closed position over the pouch 12. It is envisioned that other types of releasable fastening means may be employed.

The pouch 12 is adapted to receive a cooling pack 14 therein such that the cooling pack 14 rests on the bottom panel 12A between the side panels 12B and such that the flap 12C covers the cooling pack 14 when the flap 12C is in a closed position over the pouch 12. The cooling pack 14 may be any conventional and well known device such as a gel package designed to retain a low temperature for a reasonably long period of time after the package has been frozen or refrigerated.

The pouch 12 is manufactured of an insulative polymer to help prevent condensation on an outside surface of the pouch 12 when the cooling pack 14 is enclosed therein. This material may be a dense rubber or vinyl, for example.

A strap 16 comprises a first section 16A and a second section 16B. The first and second sections 16A, 16B are attached to opposite ends of the pouch 12. A first fastener 18 is attached to the first section 16A near a first section distal end 16C. A second fastener 20 is configured to mate with the first fastener 18 and is attached to the second section 16B near a second section distal end 16D. The first and second fasteners 13, 20 may be hook and loop fasteners as shown, or any other conventional, adjustable fastening system.

Figure 2:
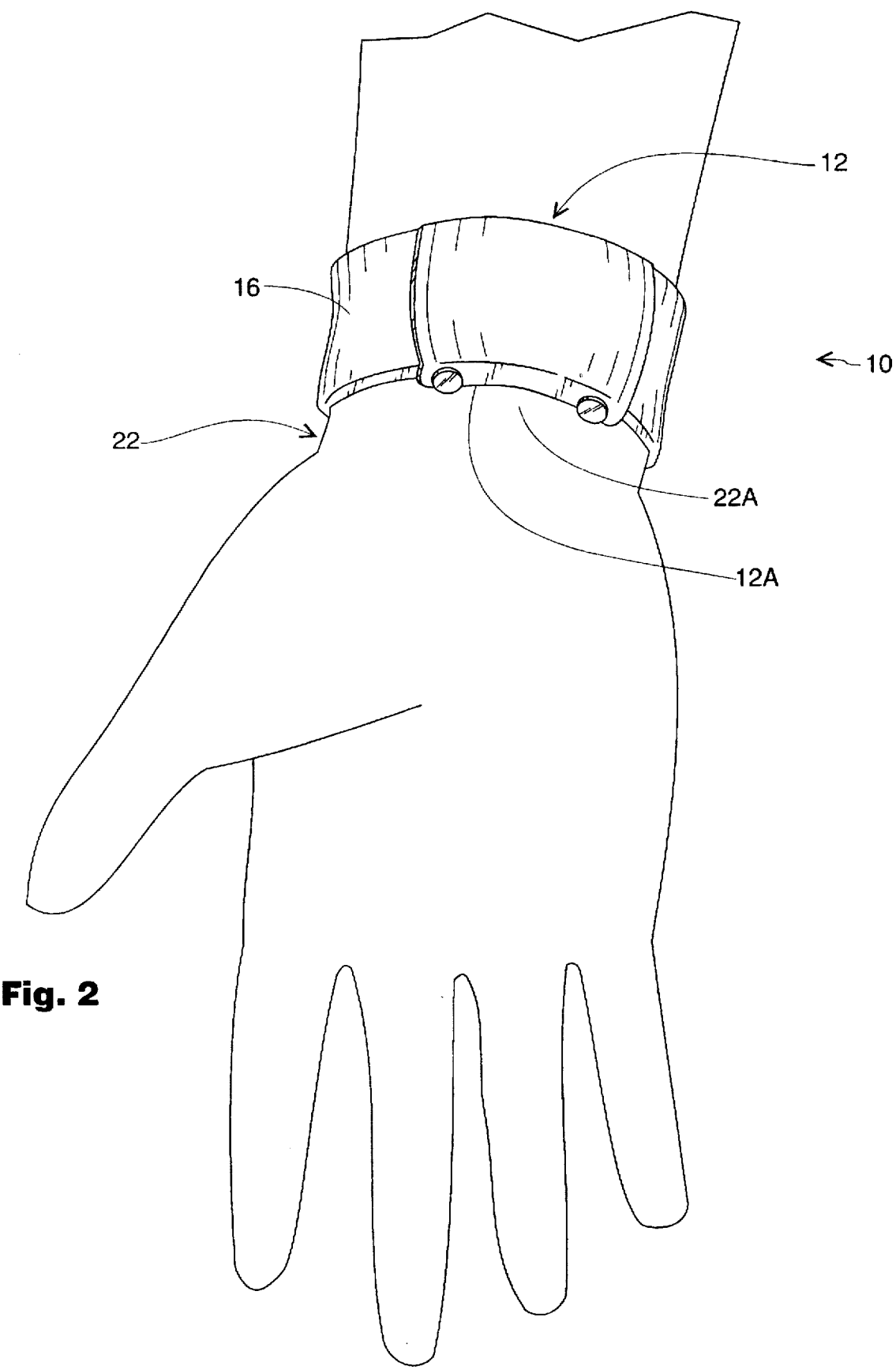
FIG. 2 is a perspective view of the cooling device worn on a human wrist.

FIG. 2 is a perspective view of the cooling device 10 worn on a human wrist 22. The strap 16 is fastened about the wrist 22, and the cooling device 10 is worn with the pouch 12 on an inside 22A of the wrist 22, such that the bottom panel 12A rests against the inside 22A of the wrist 22. By applying the cool pouch 12 of the cooling device 10 to the inside 22A of the wrist 22, a significant cooling effect to the body is promoted. It is envisioned that the cooling device 10 could be adapted to provide cooling to other appendages and areas of the body, as well.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. The scope of the invention is to be limited only by the following claims and their legal equivalents.

The invention claimed is:

1. A cooling device comprising:
   a. a shallow, generally box shaped pouch consisting of:
      i. a broad, planar, bottom panel;
      ii. at least one narrow side wall extending outwardly from the bottom panel;
      iii. the at least one narrow side wall forming a single planar opening directly opposite and parallel to the bottom panel;
      iv. and a flap consisting of a broad, planar member hingedly connected to one of the at least one narrow side walls such that the planar member is able to alternately cover and uncover the opening, and a fastening means attached to a distal end of the planar member for releasably fastening the flap to one of the at least one narrow side walls when the planar member is covering the opening;
   b. the pouch adapted to receive a cooling pack therein through the opening such that the cooling pack rests against the bottom panel between the bottom panel and the opening;
   c. a strap comprising a first section and a second section, the first and second sections attached to opposite ends of the pouch;
   d. the strap having a strap fastening means adapted to releasably fasten the strap about a human wrist such that the bottom panel rests against an inside of the wrist; and
   e. the cooling device adapted to permit the cooling pack to be alternately placed in and removed from the pouch by moving the cooling pack in a direction generally perpendicular to the bottom panel and through the opening while the strap is fastened about the wrist and the bottom panel rests against an inside of the wrist.

2. The cooling device of claim 1, wherein the pouch is constructed of an insulative polymer.

3. The cooling device of claim 1, wherein the strap fastening means comprises a first fastener attached to the first section near a first section distal end and a second fastener configured to mate with the first fastener and attached to the second section near a second section distal end.

* * * * *